United States Patent
Weisman et al.

(10) Patent No.: US 9,610,242 B2
(45) Date of Patent: Apr. 4, 2017

(54) WATER-GEL EMULSION COMPOSITIONS AND METHODS

(71) Applicant: Concept Laboratories, Inc., Chicago, IL (US)

(72) Inventors: Zoe Weisman, Chicago, IL (US); Jose Torres, Chicago, IL (US)

(73) Assignee: Concept Labs, Inc., Chicago, IL (US)

( * ) Notice: Subject to any disclaimer, the term of this patent is extended or adjusted under 35 U.S.C. 154(b) by 2 days.

(21) Appl. No.: 14/832,765

(22) Filed: Aug. 21, 2015

(65) Prior Publication Data

US 2017/0049691 A1 Feb. 23, 2017

Related U.S. Application Data

(60) Provisional application No. 62/206,703, filed on Aug. 18, 2015.

(51) Int. Cl.
| | |
|---|---|
| *A61K 8/97* | (2006.01) |
| *A61K 8/67* | (2006.01) |
| *A61K 8/898* | (2006.01) |
| *A61K 8/34* | (2006.01) |
| *A61Q 19/00* | (2006.01) |
| *A61K 8/81* | (2006.01) |

(52) U.S. Cl.
CPC ............... *A61K 8/975* (2013.01); *A61K 8/34* (2013.01); *A61K 8/342* (2013.01); *A61K 8/676* (2013.01); *A61K 8/8141* (2013.01); *A61K 8/8158* (2013.01); *A61K 8/898* (2013.01); *A61K 8/97* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 4,363,886 | A * | 12/1982 | Lipowski | C02F 1/54 523/336 |
| 4,525,496 | A | 6/1985 | Adaway et al. | |
| 4,673,704 | A | 6/1987 | Flesher et al. | |
| 4,933,179 | A * | 6/1990 | Allison | A61K 9/1075 424/207.1 |
| 5,612,021 | A * | 3/1997 | Mellul | A61K 8/19 424/401 |
| 5,935,584 | A | 8/1999 | Guerrero et al. | |
| 5,981,578 | A | 11/1999 | Alexandrides | |
| 6,464,987 | B1 * | 10/2002 | Fanara | A61K 9/0019 424/400 |
| 6,585,984 | B1 | 7/2003 | Scott et al. | |
| 6,987,195 | B2 | 1/2006 | Pereira et al. | |
| 7,217,424 | B2 | 5/2007 | Pereira et al. | |
| 7,396,526 | B1 * | 7/2008 | Cole | A61K 8/365 424/400 |
| 7,429,625 | B2 | 9/2008 | Harrington et al. | |
| 2002/0193321 | A1 | 12/2002 | Vishnupad et al. | |
| 2003/0161852 | A1 | 8/2003 | Miller et al. | |
| 2003/0211126 | A1 | 11/2003 | Fitzpatrick et al. | |
| 2005/0019291 | A1 * | 1/2005 | Zolotarsky | A61K 8/0208 424/70.11 |
| 2006/0093569 | A1 | 5/2006 | Belmar et al. | |
| 2006/0147390 | A1 * | 7/2006 | Schreiber | A61K 8/046 424/47 |
| 2006/0198800 | A1 * | 9/2006 | Dilallo | A61K 8/0212 424/59 |
| 2008/0216948 | A1 | 9/2008 | Delehanty et al. | |
| 2009/0134551 | A1 | 5/2009 | Delehandy et al. | |
| 2009/0291148 | A1 * | 11/2009 | Breyfogle | A61K 8/19 424/641 |
| 2009/0297461 | A1 | 12/2009 | Perle et al. | |
| 2010/0144961 | A1 | 6/2010 | Delehanty et al. | |

(Continued)

FOREIGN PATENT DOCUMENTS

| | | |
|---|---|---|
| EP | 1047399 A1 | 11/2000 |
| EP | 1192939 A2 | 4/2002 |

(Continued)

OTHER PUBLICATIONS www.theherbarie.com/files/resource-center/formulating/Emulsifiers_HLB_Values.pdf availabel Mar. 1, 2013.*
ViscOptima™ LV Product Details, Croda International Plc or Croda, Inc., available at http://www.croda.com/home.aspx?view=dtl&d=content&s=157&r=273&p=1859&productName=Visc&inciname=&chemicaltype=&application=&subapplication=&productfunction=&consumerbenefit=&prodID=1897, last visited Mar. 21, 2013.
ViscOptima™ SE Product Details, Croda International Plc or Croda, Inc., available at http://www.croda.com/home.aspx?view=dtl&d=content&s=157&r=273&p=1859&productName=Visc&inciname=&chemicaltype=&application=&subapplication=&productfunction=&consumerbenefit=&prodID=1894, last visited Mar. 21, 2013.
ViscOptima™ PL, Product Details, Croda International Plc or Croda, Inc., available at http://www.croda.com/home.aspx?view=dtl&d=content&s=157&r=273&p=1859&productName=Visc&inciname=&chemicaltype=&application=&subapplication=&productfunction=&consumerbenefit=&prodID=1609, last visited Mar. 21, 2013.

(Continued)

*Primary Examiner* — Robert A Wax
*Assistant Examiner* — Caralynne Helm
(74) *Attorney, Agent, or Firm* — Beem Patent Law Firm

(57) ABSTRACT

A water-based composition containing oil soluble components may include an anhydrous concentrate and a hydration component, which may be stored in separate vessels prior to mixing. The anhydrous concentrate may be combined with the hydration component to create a consumer product such as a topical cream. The anhydrous concentrate may include a preparation that includes a liquid dispersion polymer, an inverting surfactant and a binding agent, and also may include lipid-soluble vitamins, antioxidants and the like. The hydration component may include water and a preservative system, and also may include water-soluble vitamins, antioxidants and the like. Two forms (i.e. lipid-soluble and water-soluble) of a given ingredient (such as vitamin C) may be provided in the concentrate and the hydration component, respectively. A third vessel may be used for mixing the concentrate with the hydrator and/or dispensing the concentrate, the hydrator and/or the consumer product.

4 Claims, 7 Drawing Sheets

(56) References Cited

U.S. PATENT DOCUMENTS

| | | | | |
|---|---|---|---|---|
| 2010/0322883 | A1* | 12/2010 | Gohier | A61K 8/25 424/63 |
| 2011/0142897 | A1* | 6/2011 | Cotton | A61K 8/8158 424/401 |
| 2011/0189249 | A1* | 8/2011 | Liu | A61K 8/06 424/401 |
| 2011/0195103 | A1* | 8/2011 | Perez Arcas | A61K 8/73 424/401 |
| 2011/0229538 | A1* | 9/2011 | Matravers | A61K 8/676 424/401 |
| 2012/0328539 | A1 | 12/2012 | Tamura et al. | |
| 2014/0275289 | A1 | 9/2014 | Weisman et al. | |

FOREIGN PATENT DOCUMENTS

| | | |
|---|---|---|
| WO | 03105798 A1 | 12/2003 |
| WO | 2008116135 A2 | 9/2008 |
| WO | 2011085278 A2 | 7/2011 |
| WO | 2011126978 A1 | 10/2011 |

OTHER PUBLICATIONS

Diocide Product Details, Centerchem, Inc., available at http://www.centerchem.com/PDFs/DIOCIDE%20Tech%20Lit%201011.pdf, last visited Mar. 21, 2013.

Phytofix Product Details, Barnet Products Corp., available at http://www.protecingredia.com/products/barnet/Phytofix.pdf, Jan. 19, 2010.

Lavandox Material Safety Data Sheet, Barnet Products Corp., available at http://www.barnetproducts.com/pdfs/msds/Lavandox.pdf, May 4, 2012.

Arophira Product Specifications, Barnet Products Corp., available at http://www.barnetproducts.com/pdfs/specs/Arophira%202007.pdf, Feb. 13, 2007.

Kathon Product Detals, Dow Chemical Company, available at http://www.dow.com/microbial/applications/kathon.htm, last visited Mar. 21, 2013.

Sepigel 305 Product Details, SEPPIC, available at http://www.seppic.com/cosmetique/polymeres-classiques/epaississant-sepigel-305-@/view-315-seproduit.html;jsessionid=el5hO6aWgGwPF1tYWALqRQ_#, last visited Mar. 21, 2013.

RapiThix™ Material Safety Data Sheet, ISP Corp., available at http://online1.ispcorp.com/MSDS/RapiThix%20A-60_EN_43002D.pdf, last visited Mar. 21, 2013.

Integrigel O/W-EHS Product Description, Integrity Ingredients Corp., available at http://www.innovadex.com/PersonalCare/Detail/4699/129135/INTEGRIGEL-O-W-EHS, last visited Mar. 21, 2013.

Crodamol™ STS Product Details, available at http://www.croda.com/home.aspx?view=dtl&d=content&s=157&r=401&p=2578&productName=STS&inciname=&application=&subapplication=&productfunction=&consumerbenefit=&prodID=603, last visited Mar. 21, 2013.

The Super Fruits Product Details, VegeTech Co., available at http://www.vegetech.com/library/Superfruits_Brochure.pdf, 2010.

Time in a Bottle, Philosophy, available at http://www.philosophy.com/skin-care-treatment/time-in-a-bottle-serum, en_US,pd.html, 2015.

Botanisil S-19 Premium Technical Data Sheet, Botanigenics, Inc., Feb. 25, 2014.

Botanisil TE-3, Material Safety Data Sheet, Botanigenics, Inc.

Botanisil TE-3, Specification Sheet, Botanigenics, Inc., Feb. 25, 2014.

ViscOptima™ SE Product Details, Croda International Plc or Croda, Inc., May 1, 2013.

Notification of Transmittal of the International Search Report and Written Opinion dated Oct. 17, 2016, issued in International Application No. PCT/US2016/047251 (10 pages).

* cited by examiner

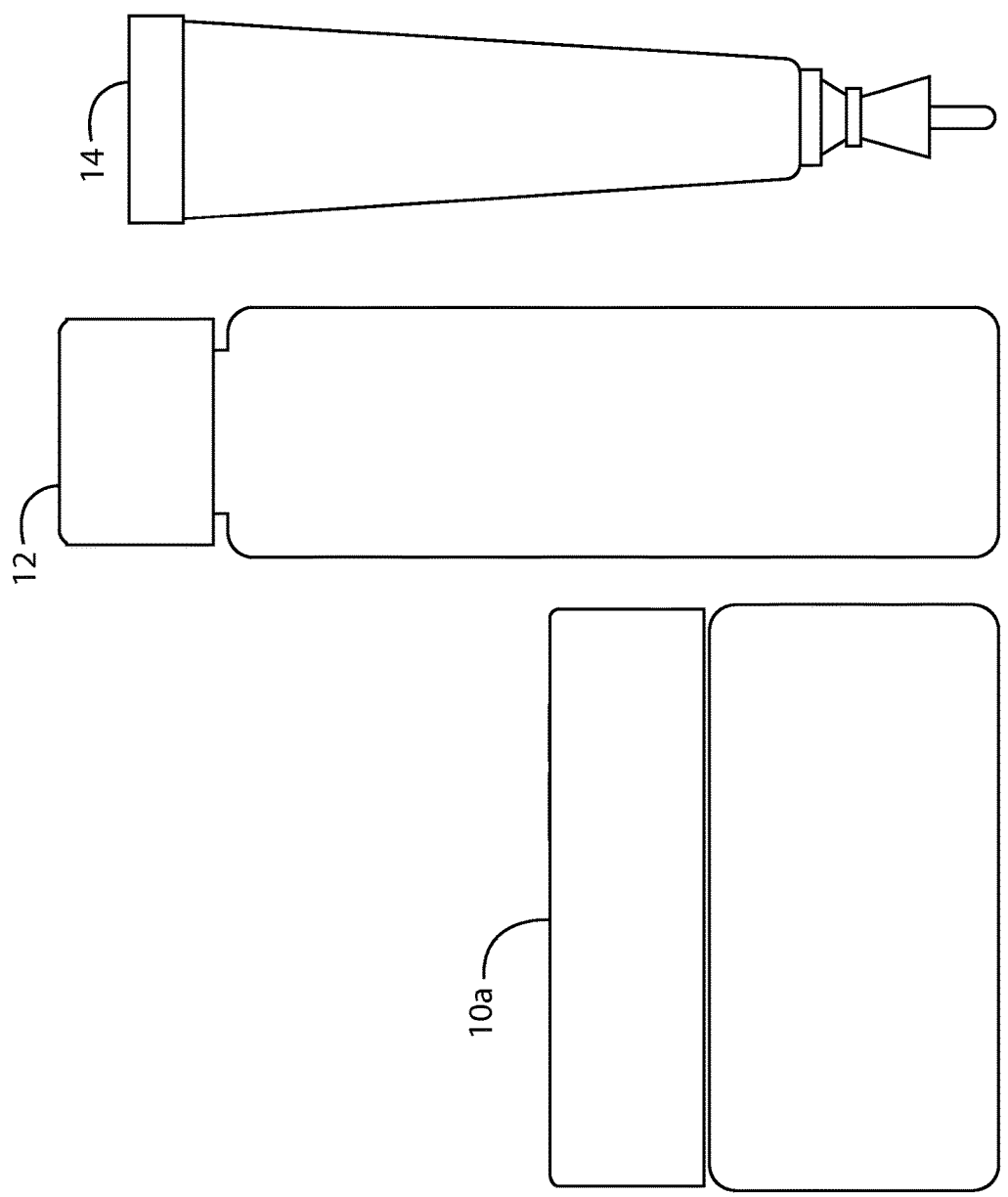

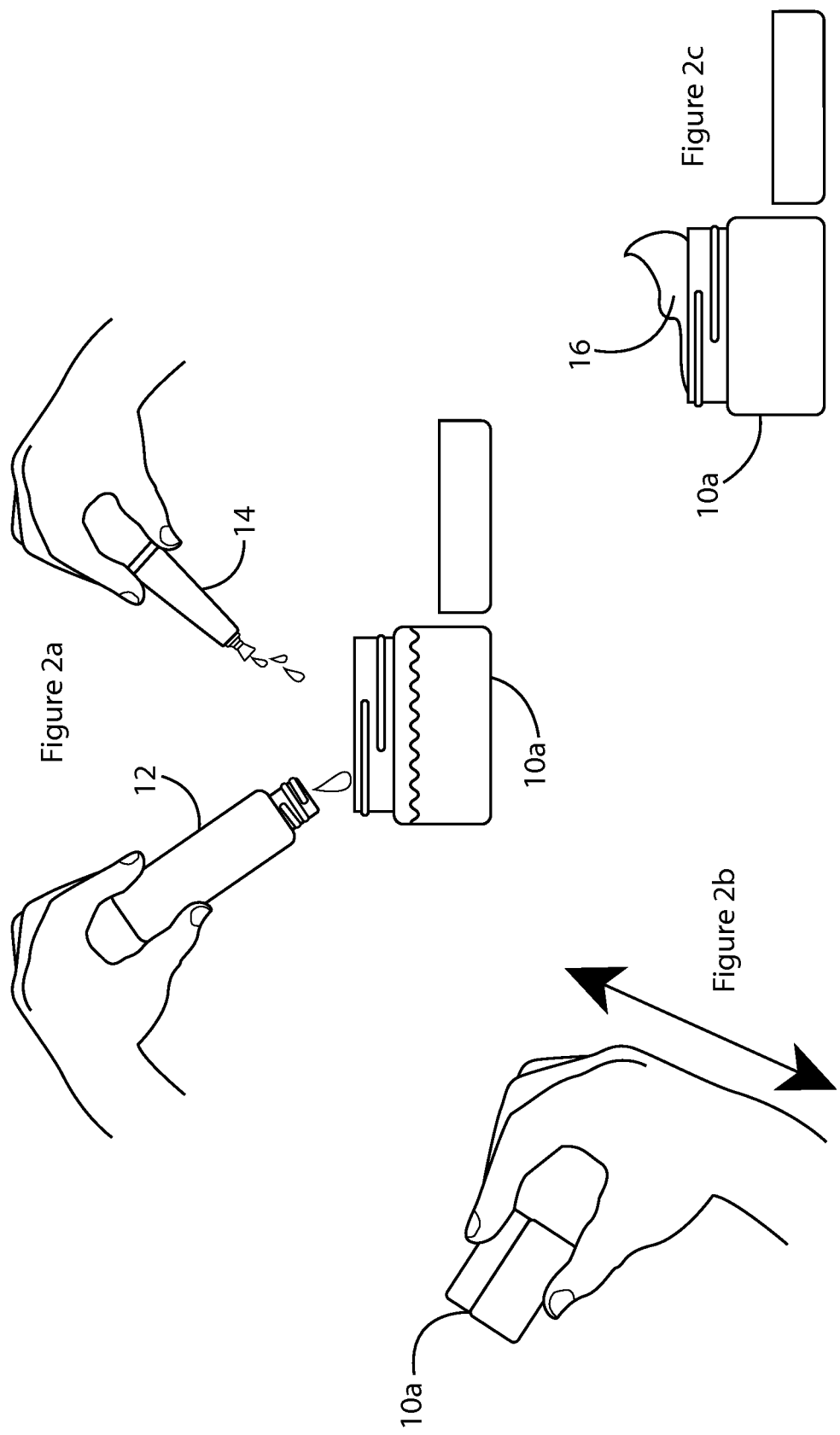

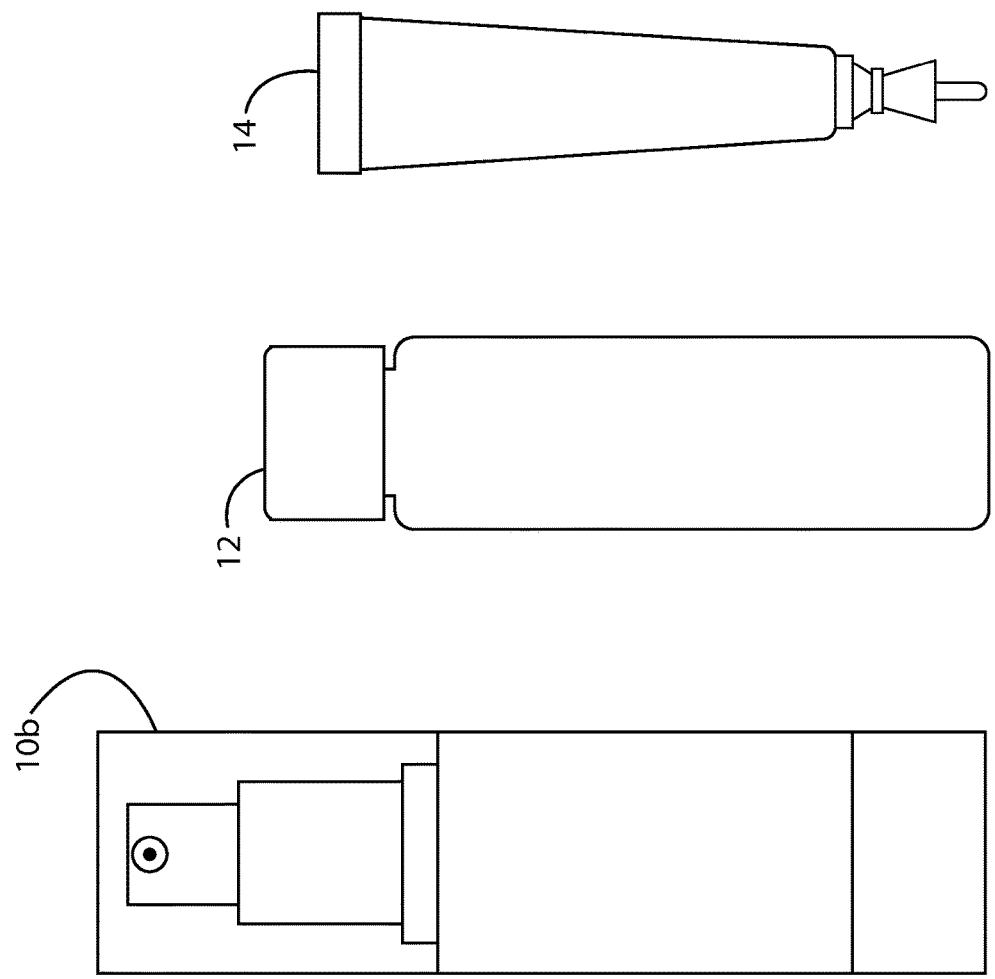

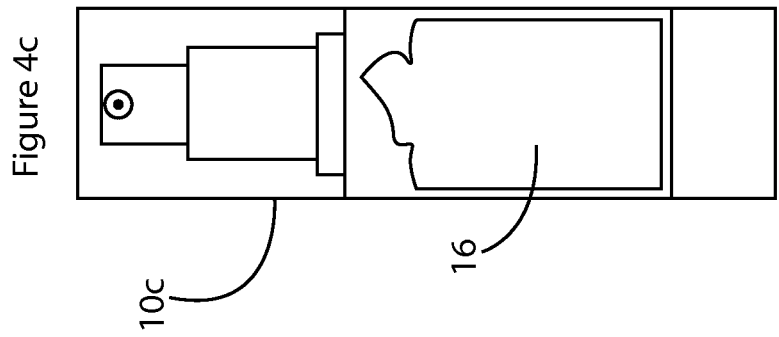
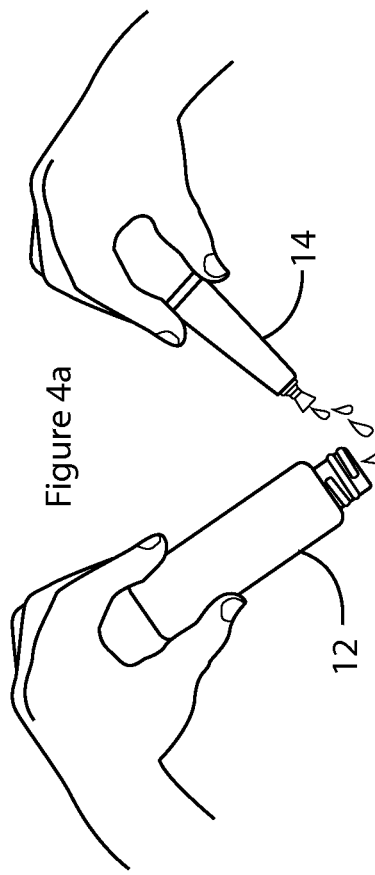
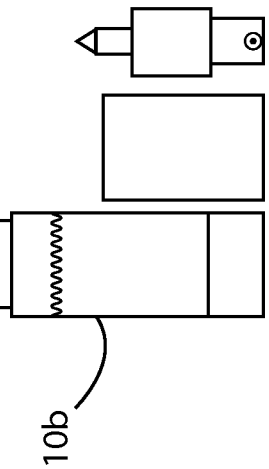
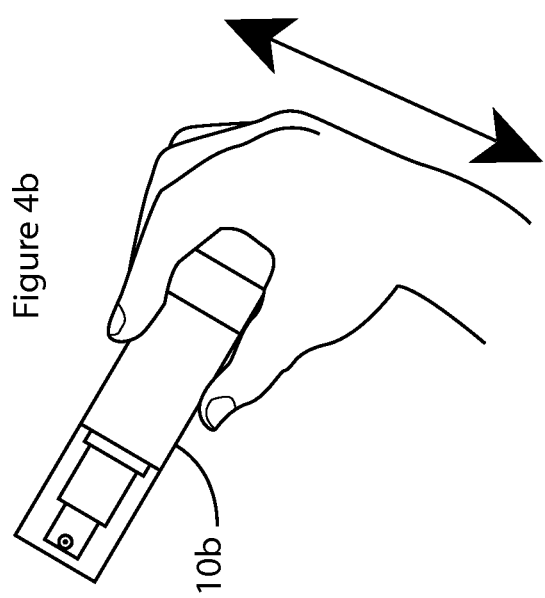

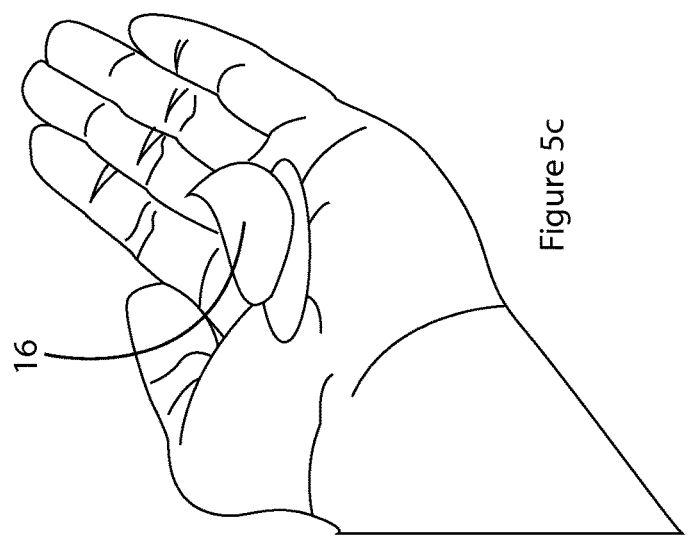
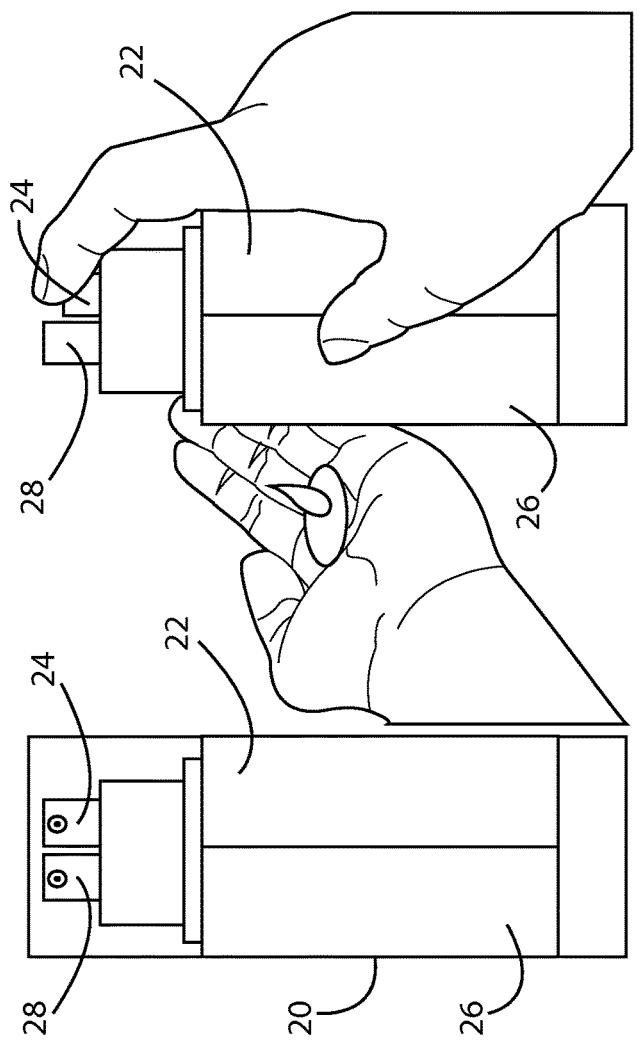

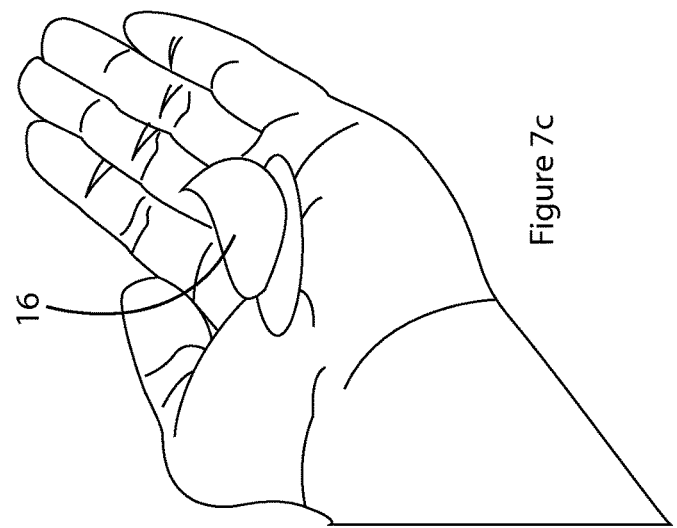
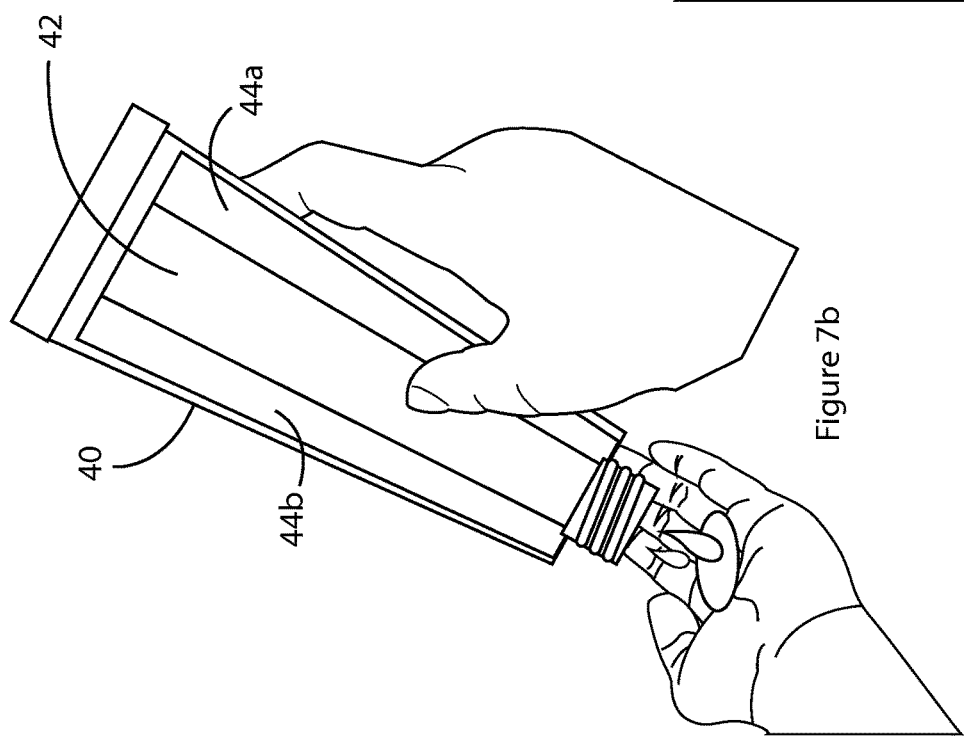
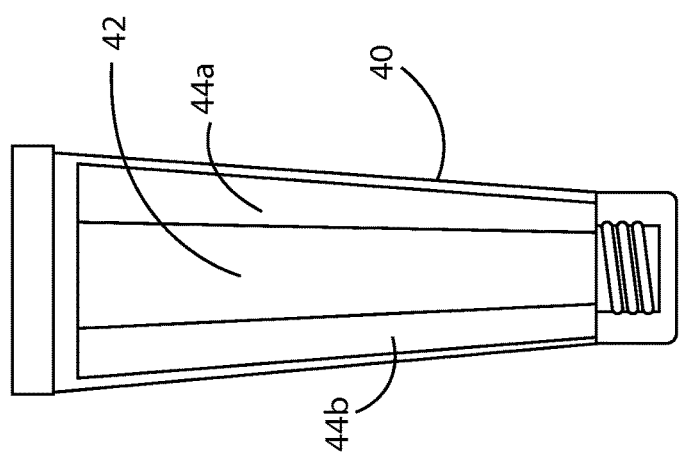

WATER-GEL EMULSION COMPOSITIONS AND METHODS

This application claims priority under 35 USC §119(e)(1) of provisional application No. 62/206,703, filed Aug. 18, 2015.

BACKGROUND OF THE INVENTION

1. Technical Field

This invention relates to an emulsion compositions and related methods and/or packaging including the composition for use in water-based consumer products, including but not limited to cosmetics.

2. Related Art

Consumers, cosmetologists, and dermatologists recognize the beneficial effects of skin care ingredients like retinol and vitamin C. These and other beneficial ingredients are among a class of unstable raw materials that are valued for their efficacy in the laboratory but are criticized in the marketplace due to their short shelf life. Commonly, exposing these ingredients to oxygen, extreme temperatures, or UV light cause the compounds to degrade and lose efficacy. Thus, the beneficial impact of the product is diminished.

To overcome these issues, cosmetic manufacturers may deliver a concentrate including various active components to an end user, who then mixes the concentrate with a predetermined amount of water to create the final product such as a jar of skin cream, such as the one described in United States Patent Publication No. 2014/0275289. This type of delivery method has several benefits for the manufacturer, such as a longer shelf-life for the product, simplified manufacturing processes, reduced material usage, reduced shipping costs, and the like. In addition, the consumer becomes an engaged member of the product creation process by mixing the concentrate with water to generate the final product. Ideally, this process can be fun for the consumer but if the emulsion process takes too long or the emulsion does not remain stable for a suitable period of time, the consumer can become frustrated and dissatisfied with the process.

Because of the unstable nature of the active components used in these formulas, it can be difficult to predict the results of a modification to an existing product. For example, certain types of emulsification methods may work for certain types of oils and vitamins while being ineffective for others. Specifically, it has been found that some types of polymer preparations and/or emulsifiers may emulsify retinol, but may not emulsify vitamin C, or vice versa. Similarly, some types of polymer preparations and/or emulsifiers may emulsify one form of an oil or vitamin but not emulsify other forms. Even seemingly subtle modifications to a formula may cause the end product to exhibit undesirable characteristics, such as an undesirable viscosity (e.g. too thick or too thin), discoloration, foaming, and the like. This problem is exacerbated by the high concentration levels at which these materials may be provided in a given concentrate. And even if a suitable emulsion is formed, separation may occur before even a small amount of composition is used, resulting in an aesthetically unpleasant and/or less effective product.

In addition, providing only an anhydrous concentrate that is mixed with water alone hinders the ability of a manufacturing to provide water-soluble components that may enhance the desirability of the end product.

Accordingly, a need has long existed for improved water-based cosmetics and methods for delivering the same.

SUMMARY

A method for making a water-based composition containing oil soluble components may include an anhydrous concentrate and a hydration component, which may be stored in separate vessels prior to mixing. The anhydrous concentrate may be combined with the hydration component to create a consumer product such as a topical cream. The anhydrous concentrate may include a preparation that includes a liquid dispersion polymer, an inverting surfactant and a binding agent. The hydration component may include water and a preservative system. The concentrate may include lipid-soluble vitamins, antioxidants and the like, and the hydration component may include water-soluble vitamins, antioxidants and the like. Two forms (i.e. lipid-soluble and water-soluble) of a given ingredient (such as vitamin C) may be provided in the concentrate and the hydration component, respectively. A third vessel, such as a jar or the like may be used for mixing the concentrate with the hydrator and/or dispensing the concentrate, the hydrator and/or the consumer product.

Other systems, methods, features and technical advantages of the invention will be, or will become apparent to one with skill in the art, upon examination of the figures and detailed description. It is intended that all such additional systems, methods, features and technical advantages be included within this summary and be protected by the claims.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1 shows an exemplary apparatus for providing a water-based consumer product;

FIGS. 2a-c show a depiction of the steps of preparing the final product for the exemplary apparatus shown in FIG. 1;

FIG. 3 shows another exemplary apparatus for providing a water-based consumer product;

FIGS. 4a-c show a depiction of the steps of preparing the final product for the exemplary apparatus shown in FIG. 3;

FIGS. 5a-c show another exemplary apparatus for providing a water-based consumer product and a depiction of the steps of preparing the final product for that exemplary apparatus;

FIGS. 7a-c show another exemplary apparatus for providing a water-based consumer product and a depiction of the steps of preparing the final product for that exemplary apparatus.

DETAILED DESCRIPTION OF THE PREFERRED EMBODIMENTS

Figure 6C:
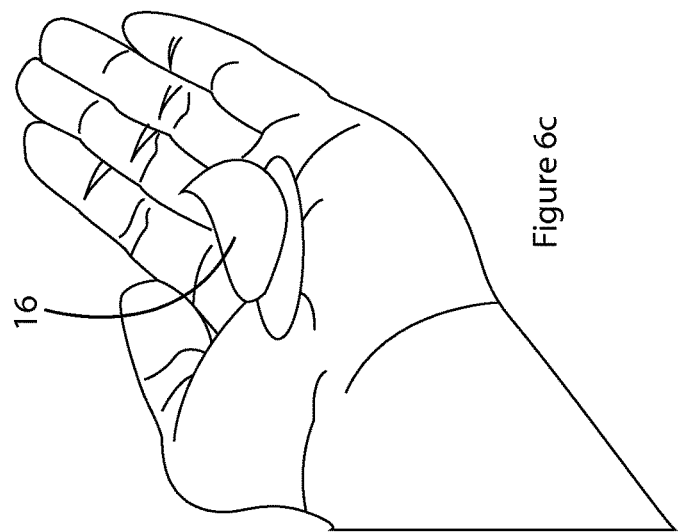
FIG. 6a-c show another exemplary apparatus for providing a water-based consumer product and a depiction of the steps of preparing the final product for that exemplary apparatus.

The elements illustrated in the figures may interoperate as explained in more detail below. Before setting forth the detailed explanation, however, it is noted that all of the discussion below, regardless of the particular implementation being described, is exemplary in nature, rather than limiting.

Referring to the drawings, and initially to FIGS. 1 and 2a-c, an apparatus or kit for delivering a water-based composition is shown. In the illustrated example, the apparatus may include a first vessel 14 for containing an anhydrous concentrate and a second vessel 12 for containing a hydration component (also referred to herein as a hydrator). The apparatus may also include a third vessel 10 in which the anhydrous concentrate and the hydration component (FIG. 2a) may be mixed by agitation (FIG. 2b), creating an end product that may be contained in and/or dispensed from the third vessel 10a (FIG. 2c).

The first vessel 14 and/or the second vessel 12 may be airtight vessels, such as ampoules, bottles, tubes and the like to ensure stability of the ingredients. In some embodiments, one or both of vessels 14 and 12 also may be opaque to insulate the concentrate and/or hyrdrator from both light and air exposure, substantially reducing degradation of the active ingredients, e.g., the antioxidants, anti-wrinkle agents and the like in the case of a cosmetic formulation. In addition, easily oxidized materials in the anhydrous concentrate (such as retinol or vitamin C) may be protected by adding nitrogen or the like to an individual vessel (e.g. ampoule or tube) prior to sealing. The manufacturer may save in material costs as the packaging required for an ampoule may be significantly smaller than that necessary for a full-sized vessel of the finished product. Similarly, the manufacturer may realize significant shipping savings.

A kit also may include a stirring device and an applicator device. Stirring device and applicator may be the same article, or the kit may include separate stirring and application components.

In order to prepare the final product, the user may remove the first vessel 14 from the packaging, open the first vessel 14, and deposit the concentrate in the third vessel 10a, as seen in FIGS. 2a-c. The user then may add the hydrator from the second vessel 14, close the third vessel, and shake for a certain length of time. As described above, the addition of mechanical energy to the concentrate may result in the formation of a stable, emulsion that is ready for use. When shaken by an individual by hand in a small jar, the shake time may be between about 3 seconds and about 20 seconds, preferably less than about 10 seconds, and even more preferably less than about 5 seconds. The may be sized to hold between about a 7 day supply and about a 60 day supply of composition, and preferably about a 30 day supply of composition.

The end-consumer may be permitted to sanitize and re-use the third vessels provided in the original apparatus to reduce waste. The supplier may then provide the end-consumer with an additional set of first and second vessels (concentrates and hydrators) rather than shipping them an entirely new third vessel and box, creating a significant waste reduction.

In some embodiments, the anhydrous concentrate may be for use in consumer products, such as cosmetics. The concentrate preferably is at least one of freeze, thaw, and temperature stable. As discussed herein, the combination of components, both active and inactive, may be considered a preparation or a concentrate.

The concentrate may include a polymer preparation having one or more liquid dispersion polymers, preferably at least one polyacrylate, as part of an anhydrous solution. In addition, the polymer preparation may include one or more esters. The polymer preparation also may include one or more ethers, which may act as surfactants. The polymer also may include one or more emollients. The combination of two or more of these components may be referred to herein as a polymer preparation.

The concentrate may also include an additional emulsifier. Preferably, the emulsifier includes a hydroxy alkyl group, such as hydroxypropylcocoate PEG-8 dimethicone. In some embodiments, the additional emulsifier may be Botanisil TE3, sold by Botanigenics of Northridge, Calif. The use of an emulsifier with a hydroxyl alkyl group may provide strong polar interactions that increase activity with water.

The concentrate may include other components, which may permit it to be customized or tailored to one or more specific uses, such as one or more lipid-soluble vitamins, anti-oxidants, minerals and the like. For example, the concentrate may include one or more lipid-soluble forms of vitamin C, such as tetrahexyldecyl ascorbate (which may be sold under the trade name "By OSC" by Barnet Products Corporation of Englewood Cliffs N.J.). The addition of lipid-soluble vitamins, minerals, and the like may add various benefits to the end product, such anti-oxidant activity, anti-wrinkle or aging effects, increased product stability, increased hydration and the like.

Other exemplary lipid-soluble vitamins and anti-oxidants may include ascorbyl palmitate, tocopherol, retinol, retinyl palmitate, salicylic acid and the like. Other lipid-soluble vitamins, anti-oxidants, minerals and the like may also be used.

In some embodiments, the concentrate contains only or substantially only oil soluble additional components. In that case, the additional components may be dissolved in the oil carrier as part of the concentrate. After the addition of the hydrator, agitation then may stimulate the formation of a gel-matrix emulsion, with the additional oil soluble ingredients being suspended within the matrix.

Each additional component of the concentrate preferably is and remains chemically separate from the other components, such that the components may not combine chemically with one another—prior to, during, or after agitation—which may allow each component to retain as much of its independent efficacy as possible.

The types and quantities of additional materials within the end product may be determined based on the purpose for which the concentrate may be used. For example, for final preparations intended to be used topically or on the hair, it may be desirable to include oil-soluble beneficial chemicals such as essential fatty acids or tamanu, kukui, lavender, monoi de Tahiti, or argan oils, as well as other components whose uses and relevant concentrations may be known or determined by those of ordinary skill in this art.

For example, in one embodiment, a silky or more luxurious feel may be desired. As such, the anhydrous solution may include one or more of a silicone, an ester, or a silicone replacement, that may act as an emollient. For example, one preferable ester that may be included is PPG-3 Benzyl Ether Myristate, which may be sold by Croda Inc. under the trademark CRODAMOL STS LQ. The concentrate may include this or other silicones, esters, or silicone replacements in order to achieve the desired feeling.

As discussed below, the formula may be prepared so that the polyacrylate polymer such as Viscoptima SE, may be dispersed in a carrier oil such as mineral oil containing an ionic or quick-inverting surfactant. Viscoptima SE is a polyacrylate polymer dispersed in an oil carrier with a surfactant. The sodium polyacrylate assists the emulsifier because it also has emulsifying properties. It aids in the inversion of the emulsion by swelling via osmosis and forming a matrix across the oil and water phases, with very little agitation.

The hydrator may include water and a preservative or preservative system to protect the hydrator from biological contamination and the like. The preservative may be selected based on the purpose for which the end product may be used. In some embodiment, the preservative may include phenoxyethanol, capryl glycol, ethylhexylglycerin and hexylene glycol, which may be sold under the trademark Botanistat PF 64 by Botanigenics of Northridge, Calif.

The hydrator may also include a solubilizer. For example, when used in cosmetic creams, the solubilizer may include PEG-12 dimethicone, which may be sold under the trademark Botanisil S19 sold by Botanigenics of Northridge, Calif. The use of PEG-12 dimethicone may contribute a luxurious feel to a finished cream by, for example, reducing tackiness and/or improving the spread and overall positive feel of the cream. PEG-12 dimethicone may be preferred because it causes reduces and/or eliminates foaming of the hydrator and provides better aesthetics to the formula and overall skin feel than other solubilizers, such as polysorbate 20 which is usually the solubilizer of choice for most cosmetic chemists.

The hydrator also may include one or more additional ingredients. The types and quantities of additional materials within the hydrator may be determined based on the purpose for which the end product may be used. Exemplary additional ingredients may include aloe vera, glycerin, humectants, hyaluronic acid, butylene glycol, glycolic acid, and the like. The hydrator also may include water-soluble vitamins, antioxidants, minerals and the like, such as ascorbic acid (preferably L-ascorbic acid), ascorbyl glucoside, 3-ethyl-ascorbic acid and the like. In some embodiments, the hydrator also may include extracts that may impart skin conditioning or fragrance. Other ingredients may also be added to the hydrator.

In embodiments including more than about 15% L-ascorbic acid, preferably a gelling agent is provided to suspend the L-ascorbic acid. If no gelling agent is provided in an embodiment having more that about 15% L-ascorbic acid, the end user may be instructed to shake prior to mixing with the oil phase. In such embodiments, an opaque or tinted (such as amber, cobalt, green and the like) second vessel 14 may be used to protect the vitamin C from UV light.

In some embodiments, similar types of ingredients may be supplied in both a lipid-soluble form in the concentrate and a water-soluble form in the hydrator. For example, a water-soluble form of vitamin C, such as L-ascorbic acid, may be added to the hydrator and an oil-soluble form of vitamin C, such as tetrahexyldecyl ascorbate, may be added to the concentrate. When using both a water-soluble and oil-soluble form of a component, synergistic effects between the two ingredients may be realized. In the above example, the water-soluble L-ascorbic acid may provide instant antioxidant benefits, while the oil-soluble tetrahexyldecyl ascorbate may provide better penetration of cellular walls, resulting in increased long-term effects.

In some embodiments, the end product may include both vitamin C and retinol. Because retinol typically is required to be at a pH of higher than 5 to be stable and most forms of vitamin C are acids that typically require a pH of below 4, the vitamin C may be provided in the hydrator and the retinol may be provided in the concentrate. The two may then be mixed just before using to provide maximum efficacy, as described below in connection with various embodiments of packaging and product delivery.

In other embodiments, pH-neutral forms of vitamin C, such as magnesium ascorbyl phosphate, sodium ascorbyl phosphate, ethyl ascorbate and the like may be added to the water phase. Because these forms of vitamin C require a suspending agent and may discolor the water, they may be dispensed in either an amber or opaque vessel to increase the desirability of the product.

The polymer preparation may remain inert until it contacts the added hydration component, at which point the sodium polyacrylate interacts with the combination of the binding agent and surfactant. Use of one or more carrier oils may affect the type of final product created, i.e., oils may be used to produce a cream rather than a gel-like feel. Conversely, substantial reduction or omission of the amount of carrier oil used, while retaining the liquid dispersion polymer, the binding agent, and the surfactant, may result in a final product being a gel or having a gel-like consistency.

Upon adding the concentrate to the hydration component and further adding mechanical energy to agitate the combination, the surfactant may emulsify the carrier fluid, and the polymer particles may swell by osmosis. A resulting polymer matrix may be created that entraps the emulsified oil, resulting in the formation of a stable emulsion.

The ratios of hydrator to concentrate may vary depending on the desired viscosity of the final product. In the case of formulations for topical application, a smaller ratio may yield a higher viscosity, resulting in a more viscous cream that may have a more occlusive, thick texture. Conversely, a larger ratio may yield a thinner cream, which may be useful in instances of lightweight lotions and the like. In some embodiments in which retinol is used, the ratio of hydrator to concentrate may be between about 5:1 and about 20:1, preferably between about 8:1 and about 12:1, and even more preferably between about 10:1 and about 11:1. In some embodiments in which vitamin C is used, the ratio of hydrator to concentrate may be between about 4:1 and about 20:1, preferably between about 8:1 and about 12:1, and even more preferably between about 9:1 and about 10:1.

In various embodiments, an apparatus for making a water-based composition containing oil soluble components may be provided. The apparatus may include a first vessel for an anhydrous concentrate including a liquid dispersion polymer, an inverting surfactant and a binding agent, and a second vessel for a hydration component including water and a preservative system. The apparatus may also include a third vessel for either (1) the first and second vessels or (2) a product formed by combining the anhydrous concentrate and the hydration component. For example, the first vessel holds between about 2 mL to about 5 mL of concentrate and the second vessel hold about 20 mL to about 50 mL of hydrator and the third vessel has a volume of between about 60 cc and about 150 cc. In some embodiments, the first vessel may be capable of being placed in a substantially airless state and at least one of the first vessel and the third vessel may be opaque or UV coated. The third vessel may dispense single dosages of either the anhydrous concentrate, the hydration component, or both.

In some embodiments, the anhydrous concentrate may include a lipid-soluble form of an ingredient, such as vitamin C, and the hydration component may include a water-soluble form of the ingredient. For example, the water-soluble form of the ingredient may be either L-ascorbic acid, magnesium ascorbyl phosphate, or both, and the lipid-soluble form of the ingredient is tetrahexyldecyl ascorbate. In some embodiments, the anhydrous concentrate may include retinol and the hydration component may include vitamin C.

The anhydrous concentrate may include sodium polyacrylate, ethylhexyl cocoate, polysorbate 20, and PPG-3 benzyl ether myristate, and/or an emulsifier that includes hydroxypropylcocoate PEG-8 dimethicone. The anhydrous concentrate also may include either an antioxidant complex, a lipid soluble vitamin, or both. The hydration component may include a solubilizer system that includes PEG-12 dimethicone.

Exemplary Polymer Preparations

Polymer Preparation Example 1

In some embodiments, the liquid dispersion polymer may include sodium polyacrylate. The preparation also may include an emollient to the preparation in order to control the aesthetic feel of the end emulsion. For example, PPG-3 benzyl ether myristate may be used as an emollient. One example of this type of polymer preparation, including relevant proportions of each, may be available commercially from Croda International Plc. or Croda Inc. in the form of a rheology modifier sold under the trademark VISCOPTIMA SE. Polymer preparation example 1 has been found to be particularly useful in formulations including retinol. Exemplary proportions of these components within the polymer preparation, and the functions for which the components are used, are provided in the following table:

TABLE 1.0

Polymer Preparation Example 1

| Chemical | Function | Percentage by weight |
| --- | --- | --- |
| Sodium Polyacrylate | Liquid Dispersion Polymer | >50% |
| Ethylhexyl Cocoate | Binding agent | 25-50% |
| Polysorbate 20 | Surfactant | 1-5% |
| PPG-3 Benzyl Ether Myristate | Emollient | 1-5% |

Polymer Preparation Example 2

In other embodiments, blends comprised of a polyacrylamide, binding agent, and/or surfactant may be used to achieve similar results. Polymer preparation example 2 has been found to be particularly useful in formulations including a lipid-soluble form of vitamin C, such as tetrahexyldecyl ascorbate. In some embodiments, the following blend, sold under the trademarks SEPIGEL 305, may be used:

TABLE 2.0

Polymer Preparation Example 2

| Chemical | Function | Percentage by weight |
| --- | --- | --- |
| Polyacrylamide | Liquid Dispersion Polymer | >50% |
| C 13-14 Isoparaffin | Emollient | 25-50% |
| Laureth-7 | Surfactant | 1-5% |

Due to the effectiveness of the polymer preparation, it may be possible to create a concentrate in which the polymer preparation is a minor component. For example, the polymer preparation may range from between about 8% to about 50% of the concentrate. After the addition of hydrator, the polymer preparation may range from about 1% to about 5% of the final product.

Exemplary Concentrates

Concentrate Examples Using Polymer Preparation Example 1

As mentioned above, the polymer preparation may be a component in a concentrate whose ultimate use may be as a topical cosmetic product. In a cosmetic product including retinol, the polymer preparation example 1 may be between about 5% and about 45% by weight of the concentrate.

In some embodiments, concentrates using polymer preparation example 1 may have the following components in the about following exemplary ratios (if the component is present):

TABLE 3.0

Example Concentrate Components

| Component | % range |
| --- | --- |
| Emollient | 27.5-42.35 |
| Polymer Preparation Example 1 | 25-27.5 |
| Retinol Complex | 2.65-6.7 |
| Antioxidant Complex | 20.00 |
| Additional Emulsifier | 10.8-18.3 |
| Meadowfoam Seed Oil | 0-10.0 |

Other ranges may also be used. For example, emollient may be provided at between about 5% and about 45% of the concentrate, preferably between about 20% and about 35%, and even more preferably between about 25% and about 30%. As another example, polymer preparation example 1 may be may be provided at between about 10% and about 45% of the concentrate, preferably between about 20% and about 35%, and even more preferably between about 25% and about 30%. A retinol complex may be provided at between about 1% and about 37% of the concentrate, preferably between about 2% and about 15%, and even more preferably between about 2.5% and about 8%. An antioxidant complex may be provided at between about 10% and about 30% of the concentrate, preferably between about 15% and about 25%, and even more preferably between about 18% and about 22%. An additional emulsifier may be provided at between about 5% and about 25% of the concentrate, preferably between about 10% and about 20%, and even more preferably between about 15% and about 18%. Finally, meadowfoam seed oil may be provided at between about 0% and about 15% of the concentrate and, if present, preferably between about 7% and about 10%.

An exemplary emollient may be PPG-3 benzyl ether myristate, which may be sold by Croda Inc. under the trademark CRODAMOL STS LQ.

An exemplary retinol complex may include about 15% retinol in caprylic/capric triglyceride, stabilized with 1% of BHT and sold under the trademark Retinol 15D by American International Chemical of Framingham, Mass.

An exemplary antioxidant complex may include *oryza sativa* (rice) bran extract, *rosmarinus officinalis* (rosemary) extract, *helianthus annuus* (sunflower) seed extract and tocopherol, which may be sold under the trademark Botanessential RRST by DD Chemco, Inc. of Chatsworth Calif.

An exemplary additional emulsifier may be hydroxypropylcocoate PEG-8 dimethicone, a water-insoluble alkyl functional silicone polyether, which may be sold under the trademark Botanisil TE-3 by Botanigenics, Inc. of Northridge, Calif.

Example 1

Concentrate

In one embodiment, an exemplary concentrate may include the following components:

TABLE 4.0

| Example 1: Concentrate | |
|---|---|
| Component | % used |
| Emollient | 27.50 |
| Polymer Preparation Example 1 | 27.50 |
| Retinol Complex | 6.70 |
| Antioxidant Complex | 20.00 |
| Additional Emulsifier | 18.30 |

To create a batch of concentrate example 1, the components may be added to a vessel in the following order: emollient, polymer preparation example 1, retinol, antioxidant complex, and additional emulsifier. Next, the components may be mixed with good agitation until they are substantially dispersed and homogeneous. Preferably, the components are at low to medium speeds to reduce and/or eliminate aeration. The resulting concentrate may be an oily liquid that is yellow and unscented. Scent may be added.

Variations of these steps, such as reordering the component additions, mixing between component additions and the like also may be performed. Similar processes may be used to prepare the other concentrate examples.

Example 2

Concentrate

In another embodiment, an exemplary concentrate may include the following components at the following levels:

TABLE 5.0

| Example 2: Concentrate | |
|---|---|
| Component | % used |
| Emollient | 27.50 |
| Polymer Preparation Example 1 | 27.50 |
| Retinol Complex | 6.70 |
| Antioxidant Complex | 20.00 |
| Meadowfoam Seed Oil | 7.50 |
| Additional Emulsifier | 10.80 |

Due to the meadowfoam seed oil present in Concentrate Example 2 (and Concentrate Example 3), the emulsification process may take longer.

Example 3

Concentrate

In another embodiment, an exemplary concentrate may include the following components at the following levels:

TABLE 6.0

| Example 3: Concentrate | |
|---|---|
| Component | % used |
| Emollient | 42.35 |
| Polymer Preparation Example 1 | 25.00 |
| Retinol Complex | 2.65 |
| Antioxidant Complex | 20.00 |
| Meadowfoam Seed Oil | 10.00 |

Concentrate Examples Using Polymer Preparation Example 2

In some embodiments, concentrates using polymer preparation example 2 may have the following components in the following exemplary ratios (if the component is present):

TABLE 7.0

| Example Concentrate Components | |
|---|---|
| Component | % range |
| Lipid-Soluble Vitamin | 20-74 |
| Polymer Preparation Example 2 | 11.1-56.51 |
| Antioxidant Complex | 7.48-40.0 |
| Additional Emulsifier | 10.000 |
| Emollient | 0-7.41 |

Other ranges may also be used. For example, lipid-soluble vitamins may be provided at between about 5% and about 75% of the concentrate, preferably between about 15% and about 30%, even more preferably between about 18% and about 25%, and in one example at about 20%. Polymer preparation example 2 may be provided at between about 10% and about 60% of the concentrate, preferably between about 25% and about 58%, and even more preferably between about 40% and about 56%. An antioxidant complex may be provided at between about 2% and about 40% of the concentrate, preferably between about 7% and about 30%, and even more preferably between about 9% and about 20%. An additional emulsifier may be provided at between about 1% and about 30% of the concentrate, preferably between about 3% and about 20%, and even more preferably between about 5% and about 15%. Finally, an emollient may be provided at between about 0% and about 15% of the concentrate, preferably between about 2% and about 10%, and even more preferably between about 3% and about 8%.

An exemplary lipid-soluble vitamin may be tetrahexyldecyl ascorbate, which may be sold under the trademark BV OSC by Barnet Products Corporation of Englewood Cliffs, N.J. An amount of the lipid-soluble vitamin may be provided in the concentrate so as to comprise between about 0.5% and about 10% of the final composition (when mixed with a hydrator), preferably between about 1% and about 6%, and even more preferably between about 2% and about 3%.

Example 4

Concentrate

In one embodiment, an exemplary concentrate may include the following components:

TABLE 8.0

| Example 4: Concentrate | |
| --- | --- |
| Component | % used |
| Lipid-Soluble Vitamin | 20.000 |
| Polymer Preparation Example 2 | 56.510 |
| Antioxidant Complex | 13.515 |
| Additional Emulsifier | 10.000 |

Example 5

Concentrate

In another embodiment, an exemplary concentrate may include the following components:

TABLE 9.0

| Example 5: Concentrate | |
| --- | --- |
| Component | % used |
| Lipid-Soluble Vitamin | 20.000 |
| Polymer Preparation Example 2 | 40.000 |
| Antioxidant Complex | 40.000 |

Example 6

Concentrate

In another embodiment, an exemplary concentrate may include the following components:

TABLE 10.0

| Example 6: Concentrate | |
| --- | --- |
| Component | % used |
| Lipid-Soluble Vitamin | 74.000 |
| Polymer Preparation Example 2 | 14.810 |
| Antioxidant Complex | 7.490 |
| Emollient | 3.700 |

Due to the high level of vitamin present in Example 6 (and Example 7), the emulsification process may take longer and the aesthetics of the final composition may be less pleasant than a composition formed with Example 1.

Example 7

Concentrate

In another embodiment, an exemplary concentrate may include the following components:

TABLE 11.0

| Example 7: Concentrate | |
| --- | --- |
| Component | % used |
| Lipid-Soluble Vitamin | 74.000 |
| Polymer Preparation Example 2 | 11.110 |
| Antioxidant Complex | 7.480 |
| Emollient | 7.410 |

Hydrator Examples

Hydrator Examples for Use with Polymer Preparation Example 1

Although the following hydrators are described as being for use with concentrates including polymer preparation example 1, such description is merely exemplary. These hydrators also may be used with concentrates including polymer preparation example 2 or other polymer preparations In some embodiments, concentrates using polymer preparation example 1 may have include one or more of following components in the following exemplary ratios (if the component is present):

TABLE 12.0

| Example Hydrator Components | |
| --- | --- |
| Component | % used |
| Water | 75-93 |
| Moisturizer 1 | 5.5-11 |
| *Aloe Vera* | 0.44-0.5 |
| Preservative System | 1.-1.1 |
| Butylene Glycol | 10.00 |
| Emulsifier | 0.25-1.0 |
| Fragrance/Extract | 0.01-1.5 |
| Emollient | 0.50 |

An exemplary moisturizer (moisturizer 1) may include water, *chondrus crispus* extract, and sodium hyaluronate, which may be sold under the trademark Marimoist by Biocogent of Stony Brook, N.Y. Another exemplary moisturizer (moisturizer 2) may include plyrus malus (apple) fruit extract and glycerin, which may be sold under the trademark Botanimoist AMS by Botanigenics, Inc. of Northridge, Calif.

Aloe vera may be provided in a gel form, such as an about 200% concentrated powder that forms a juice when combined with water.

An exemplary preservative system may include phenoxyethanol, capryl glycol, ethylhexylglycerin and hexylene glycol, which may be sold under the trademark Botanistat PF 64 by Botanigenics of Northridge, Calif.

An exemplary emulsifier may be a copolymer of a polydimethylsiloxane and a polyoxyalkylene ether, such as PEG-12 dimethicone, which may be sold under the trademark Botanisil S-19 Premium by Botanigenics, Inc. of Northridge, Calif.

Exemplary fragrances/extracts may include, for example, essential plant extracts that may provide a beneficial fragrance. In some embodiments, one or more of the following fragrances may be used: Hydroessential *Citrus Limon* 20.3709 (Fragrance 1), Hydroessential *Lavandula* 20.3031 (Fragrance 2) sold by Vevy Europe S.p.A. of Genova, Italy; Juicy Lemon Fragrance 91-1030-97 (Fragrance 3) sold by The Lebermuth Co. of South Bend, Ind.; Lavender Oil 40/42 (Fragrance 4) sold by The Lebermuth Co. of South Bend, Ind.; Hydroprime Lavender LAQ (Fragrance 5) sold by MeL-Co of Hobbs, N. Mex.

An exemplary emollient may be caprylyl methicone, which may be sold under the trademark Botanisil CPM 10 by Botanigenics of Northridge, Calif.

Ranges other than those specified in Table 12.0 also may be used. For example, water may be provided at between about 65% and about 99% of the hydrator, and preferably between about 75% and about 93%. Moisturizer 1 may be provided at between about 0% and about 80% of the hydrator, preferably between about 2% and about 20%, and even more preferably between about 4% and about 15%. Aloe vera may be provided at between about 0% and about 1.5% of the hydrator, preferably between about 0.1% and about 1.3%, and even more preferably between about 1% and about 1.1%. Preservative may be provided at between about 0.5% and about 2% of the concentrate, preferably between about 0.8% and about 1.5%, and even more preferably between about 1% and about 1.2%. Butylene glycol may be provided at between about 0% and about 20% of the hydrator, preferably between about 5% and about 15%, and in one example at about 10%. Emulsifier may be provided at between about 0% and about 2% of the hydrator, preferably between about 0.1% and about 1.5%, and even more preferably between about 0.25% and about 1%. Fragrance may be provided at between about 0% and about 2% of the hydrator and preferably between about 0.01% and about 1.5%. Finally, emollient may be provided at between about 0% and about 2% of the hydrator, preferably between about 0.1% and about 1.5%, and even more preferably between about 0.4% and about 0.75%.

Example 8

Hydrator

In one embodiment, an exemplary hydrator may include the following components:

TABLE 13.0

Example 8: Hydrator

| Component | % used |
|---|---|
| Water | 76.79 |
| Moisturizer | 11.00 |
| *Aloe Vera* 200x | 0.44 |
| Preservative System | 1.10 |
| Butylene Glycol | 10.00 |
| Emulsifier | 0.65 |
| Fragrance 1 | 0.01 |
| Fragrance 2 | 0.01 |

An exemplary process for creating a batch of hydrator example 1 will now be explained. First, the water, and preferably deionized water, may be added to a tank, followed by the moisturizer and aloe vera. Next, the components may be mixed with good agitation until they are substantially dispersed and homogeneous. Then, a premix of the preservative system and the butylene glycol is prepared in which the components may be mixed with good agitation until they are substantially dispersed and homogeneous. The emulsifier may then be added to the premix and the components again may be mixed with good agitation until they are substantially homogeneous. Next, the premix may be added to the tank and the mixture may be mixed with good agitation until the components are substantially homogeneous. Finally, the fragrances may be added to the mixture, one at a time, mixing the resulting mixture with good agitation until the components substantially homogenous between each addition. The resulting hydrator may be a liquid that is clear to slightly hazy in appearance, a citrus/floral smell and a pH of about 5.0 to about 5.5.

Variations of these steps, such as reordering the component additions, mixing between component additions and the like also may be performed. Similar processes may be used to prepare the other hydrator examples

Example 9

Hydrator

In one embodiment, an exemplary hydrator may include the following components:

TABLE 14.0

Example 9: Hydrator

| Component | % used |
|---|---|
| Water | 76.80 |
| Marimoist | 11.00 |
| *Aloe Vera* 200x | 0.44 |
| Preservative | 1.10 |
| Butylene Glycol | 10.00 |
| Emulsifier | 0.65 |
| Fragrance 1 | 0.01 |

Example 10

Hydrator

In one embodiment, an exemplary hydrator may include the following components:

TABLE 15.0

Example 10: Hydrator

| Component | % used |
|---|---|
| Water | 76.80 |
| Moisturizer 1 | 11.00 |
| *Aloe Vera* 200x | 0.44 |
| Preservative System | 1.10 |
| Butylene Glycol | 10.00 |
| Emulsifier | 0.65 |
| Fragrance 2 | 0.01 |

Example 11

Hydrator

In one embodiment, an exemplary hydrator may include the following components:

TABLE 16.0

| Example 11: Hydrator | |
|---|---|
| Component | % used |
| Water | 76.80 |
| Moisturizer 1 | 11.00 |
| Aloe Vera 200x | 0.50 |
| Preservative System | 1.10 |
| Butylene Glycol | 10.00 |
| Emulsifier | 0.75 |
| Fragrance 3 | 0.10 |

Example 12

Hydrator

In one embodiment, an exemplary hydrator may include the following components:

TABLE 17.0

| Example 12: Hydrator | |
|---|---|
| Component | % used |
| Water | 76.89 |
| Moisturizer 1 | 11.00 |
| Aloe Vera 200x | 0.50 |
| Preservative System | 1.10 |
| Butylene Glycol | 10.00 |
| Emulsifier | 0.50 |
| Fragrance 4 | 0.10 |

Example 13

Hydrator

In one embodiment, an exemplary hydrator may include the following components:

TABLE 18.0

| Example 13: Hydrator | |
|---|---|
| Component | % used |
| Water | 75.45 |
| Moisturizer 1 | 11.00 |
| Aloe Vera 200x | 0.50 |
| Preservative System | 1.10 |
| Butylene Glycol | 10.00 |
| Emulsifier | 0.45 |
| Fragrance 5 | 1.50 |

Example 14

Hydrator

In one embodiment, an exemplary hydrator may include the following components:

TABLE 19.0

| Example 14 Hydrator | |
|---|---|
| Component | % used |
| Water | 74.40 |
| Moisturizer 1 | 11.00 |
| Aloe Vera 200x | 0.50 |
| Preservative System | 1.10 |
| Butylene Glycol | 10.00 |
| Emulsifier | 3.00 |

The presence of the emollient may improve the overall aesthetics of the hydrator and/or final composition.

Example 15

Hydrator

In one embodiment, an exemplary hydrator may include the following components:

TABLE 20.0

| Example 15: Hydrator | |
|---|---|
| Component | % used |
| Water | 85.90 |
| Moisturizer 1 | 11.00 |
| Aloe Vera 200x | 0.50 |
| Preservative System | 1.10 |
| Emollient | 0.50 |
| Emulsifier | 1.00 |

Example 16

Hydrator

In one embodiment, an exemplary hydrator may include the following components:

TABLE 21.0

| Example 16: Hydrator | |
|---|---|
| Component | % used |
| Water | 87.13 |
| Moisturizer 1 | 11.00 |
| Aloe Vera 200x | 0.50 |
| Preservative System | 1.10 |
| Emulsifier | 0.275 |

Example 17

Hydrator

In one embodiment, an exemplary hydrator may include the following components:

TABLE 22.0

| Example 17: Hydrator | |
| --- | --- |
| Component | % used |
| Water | 92.63 |
| Moisturizer 1 | 5.50 |
| Aloe Vera 200x | 0.50 |
| Preservative System | 1.10 |
| Emulsifier | 0.275 |

Example 18

Hydrator

In one embodiment, an exemplary hydrator may include the following components:

TABLE 23.0

| Example 18: Hydrator | |
| --- | --- |
| Component | % used |
| Water | 87.13 |
| Moisturizer 2 | 11.00 |
| Aloe Vera 200x | 0.50 |
| Preservative System | 1.10 |
| Emulsifier | 0.275 |

Example 19

Hydrator

In one embodiment, an exemplary hydrator may include the following components:

TABLE 24.0

| Example 19 Hydrator | |
| --- | --- |
| Component | % used |
| Water | 92.75 |
| Moisturizer 2 | 5.50 |
| Aloe Vera 200x | 0.50 |
| Preservative System | 1.00 |
| Emulsifier | 0.250 |

Example 20

Hydrator

In one embodiment, an exemplary hydrator may include the following components:

TABLE 25.0

| Example 20: Hydrator | |
| --- | --- |
| Component | % used |
| Water | 67.891 |
| Moisturizer 2 | 5.000 |
| Aloe Vera 200x | 0.387 |
| L-Ascorbic Acid Micronized | 15.000 |
| Preservative System | 1.100 |
| Butylene Glycol | 10.000 |
| Emulsifier | 0.650 |
| Fragrance 1 | 0.010 |
| Fragrance 2 | 0.010 |

Example 21

Hydrator

In one embodiment, an exemplary hydrator may include the following components:

TABLE 26.0

| Example 21: Hydrator | |
| --- | --- |
| Component | % used |
| Water | 62.913 |
| Moisturizer 2 | 5.000 |
| Aloe Vera 200x | 0.317 |
| L-Ascorbic Acid Micronized | 20.000 |
| Preservative System | 1.100 |
| Butylene Glycol | 10.000 |
| Emulsifier | 0.650 |
| Fragrance 1 | 0.010 |
| Fragrance 2 | 0.010 |

Hydrators for Use with Polymer Preparation Example 2

Although the following hydrators are described as being for use with concentrates including polymer preparation example 2, such description is merely exemplary. These hydrators also may be used with concentrates including polymer preparation example 1 or other polymer preparations.

TABLE 27.0

| Example Hydrator Components | |
| --- | --- |
| Component | % used |
| Water | 76-78 |
| Magnesium Ascorbyl Phosphate | 5.000 |
| Moisturizer 2 | 5.000 |
| Moisturizer 1 | 11.000 |
| Aloe Vera 200x | 0.387-0.44 |
| Preservative System | 1.100 |
| Butylene Glycol | 10.000 |
| Emulsifier | 0.65-1 |

TABLE 27.0-continued

Example Hydrator Components

| Component | % used |
|---|---|
| Fragrance 1 | 0.010 |
| Fragrance 2 | 0.010 |

Ranges other than those specified in Table 25.0 also may be used. For example, water may be provided at between about 65% and about 99% of the hydrator, and preferably between about 75% and about 93%. Magnesium ascorbyl phosphate may be provided at between about 0% and about 10% of the hydrator, preferably between about 2% and about 8%, and even more preferably between about 4% and about 6%. Moisturizer 2 may be provided at between about 0% and about 80% of the hydrator, preferably between about 2% and about 20%, and even more preferably between about 4% and about 15%. Moisturizer 1 may be provided at between about 0% and about 80% of the hydrator, preferably between about 2% and about 20%, and even more preferably between about 4% and about 15%. Aloe vera may be provided at between about 0% and about 1.5% of the hydrator, preferably between about 0.1% and about 1.3%, and even more preferably between about 0.3% and about 0.6%. Preservative may be provided at between about 0.5% and about 2% of the concentrate, preferably between about 0.8% and about 1.5%, and even more preferably between about 1% and about 1.2%. Butylene glycol may be provided at between about 0% and about 20% of the hydrator, preferably between about 5% and about 15%, and in one example at about 10%. Emulsifier may be provided at between about 0% and about 2% of the hydrator, preferably between about 0.1% and about 1.5%, and even more preferably between about 0.5% and about 1%. Finally, fragrance(s) may be provided at between about 0% and about 2% of the hydrator and preferably between about 0.01% and about 1.5%.

Example 22

Hydrator

In one embodiment, an exemplary hydrator may include the following components:

TABLE 28.0

Example 22: Hydrator

| Component | % used |
|---|---|
| Water | 76.790 |
| Moisturizer 1 | 11.000 |
| Aloe Vera 200x | 0.440 |
| Preservative System | 1.100 |
| Butylene Glycol | 10.000 |
| Emulsifier | 0.650 |
| Fragrance 1 | 0.010 |
| Fragrance 2 | 0.010 |

Example 23

Hydrator

In one embodiment, an exemplary hydrator may include the following components:

TABLE 29.0

Example 23: Hydrator

| Component | % used |
|---|---|
| Water | 77.493 |
| Magnesium Ascorbyl Phosphate | 5.000 |
| Moisturizer 2 | 5.000 |
| Aloe Vera 200x | 0.387 |
| Preservative System | 1.100 |
| Butylene Glycol | 10.000 |
| Emulsifier | 1.000 |
| Fragrance 1 | 0.010 |
| Fragrance 2 | 0.010 |

The presence of Magnesium Ascorbyl Phosphate may increase the time of the emulsification process up to about 20 seconds and/or alter the physical appearance of the hydrator.

Exemplary Combinations of Concentrates and Hydrators

The previous exemplary concentrates and hydrators may be combined in various combinations, typically at a ratio of hydrator to concentrate at about 10:1. For example, concentrates of either example 1 or example 2 preferably may be combined with any of hydrators of examples 8-10 or 20-21. As another example, the concentrate of example 3 preferably may be combined with any of the hydrators of examples 10-19. As still a further example, concentrates of either of examples 4-7 preferably may be combined with any of the hydrators of examples 22-23. These combinations are merely exemplary and other combinations of concentrates and hydrators also may be used.

Exemplary Final Product

When about 3 mL of the concentrate of example 1 is mixed with about 30 mL of the hydrator of example 8 and agitated (e.g. shaken) for about 5 second, a stable emulsions of about 30 grams of a cream having a white to off-white color, a pH of about 5.5, a specific gravity of about 1.0 and a citrus, floral odor is formed. The cream may remain stable for at least 30 days. A consumer may apply about 1 gram of the cream topically, once daily, preferably at night. The cream may possess the following components:

TABLE 30.0

Exemplary Final Product Formulation

| INCI Name: | Originating Component: | % |
|---|---|---|
| Aloe Barbadensis Leaf Juice | Aloe Vera and Water | 78.8481 |
| Butylene Glycol | Butylene Glycol | 8.9550 |
| PPG-3 Benzyl Ether Myristate | Polymer Preparation Example 1 and Emollient | 2.9563 |
| Hydroxypropylcocoate PEG-8 Dimethicone | Additional Emulsifier | 1.8300 |
| Sodium Polyacrylate | Polymer Preparation Example 1 | 1.4300 |
| Oryza Sativa (Rice) Bran Extract | Antioxidant Complex | 1.4000 |
| Ethylhexyl Cocoate | Polymer Preparation Example 1 | 1.0313 |
| Retinol | Retinol Complex | 0.1005 |

TABLE 30.0-continued

Exemplary Final Product Formulation

| INCI Name: | Originating Component: | % |
|---|---|---|
| *Chondrus Crispus* Extract | Moisturizer | 0.5940 |
| Sodium Hyaluronate | Moisturizer | 0.0099 |
| Citrus Limon Fruit Extract | Fragrance 1 | 0.0090 |
| *Lavandula Angustifolia* Flower/Leaf/Stem Extract | Fragrance 2 | 0.0090 |
| *Helianthus Annuus* (Sunflower) Extract | Antioxidant Complex | 0.2000 |
| *Rosmarinus Officinalis* (Rosemary) Leaf Extract | Antioxidant Complex | 0.2000 |
| Tocopherol | Antioxidant Complex | 0.2000 |
| PEG-12 Dimethicone | Emulsifier | 0.5850 |
| Polysorbate 20 | Polymer Preparation Example 1 | 0.0825 |
| Caprylic/Capric Triglyceride | Retinol Complex | 0.5695 |
| Phenoxyethanol | Preservative | 0.4950 |
| Caprylyl Glycol | Preservative | 0.2475 |
| Ethyl hexylglycerin | Preservative | 0.1238 |
| Hexylene Glycol | Preservative | 0.1238 |

Other percentages may also be used. For example, another exemplary composition including some of the components above may include between about 0.1% and about 1% retinol, between about 1% and about 2% sodium polyacrylate, between about 1% and about 3% hydroxypropylcocoate PEG-8 dimethicone, between about 0.5% and about 2% binding agent, between about 0.05% and about 0.12% surfactant, between about 1% and about 5% emollient, between about 0.5% and about 4% antioxidant complex, and at least about 60% water. An another example, a composition may include between about 0.5% and about 5% vitamin C, between about 1% and about 4% polyacrylamide, between about 0.25% and about 3% hydroxypropylcocoate PEG-8 dimethicone, between about 0.05% and about 0.12% surfactant, between about 0.5% and about 2% emollient, between about 0.5% and about 4% antioxidant complex, and at least about 60% water.

Packaging, Distribution, and Use

Figure 6B:
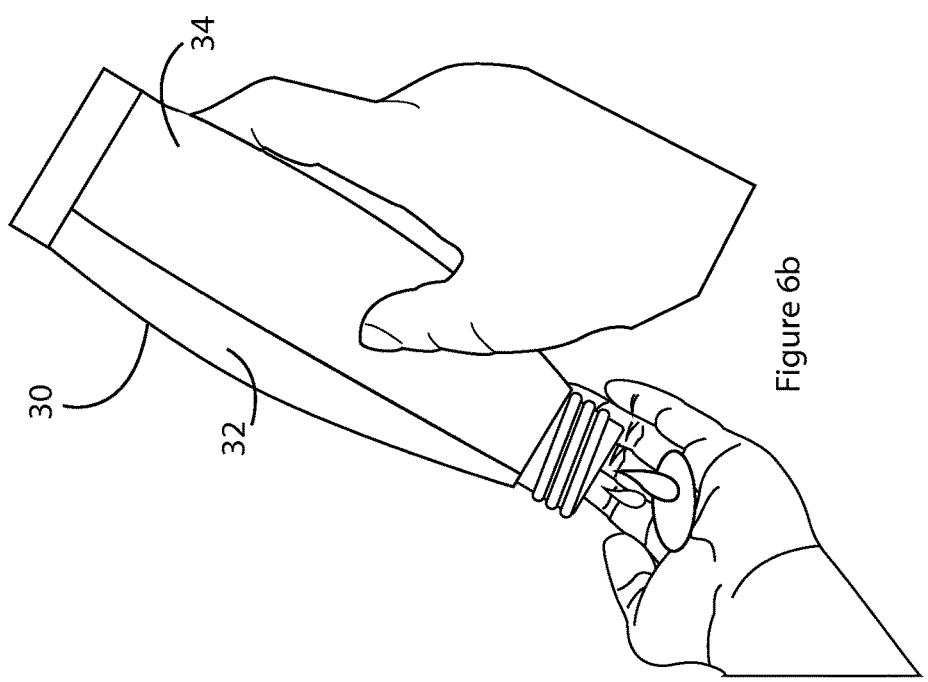
Figure 6A:
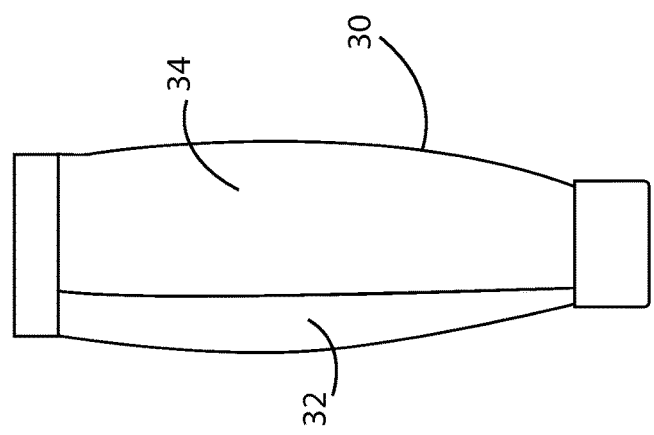

FIGS. 3-7a-c show other embodiments of apparatuses for providing water-based consumer products and depictions of the steps of preparing the final product with each exemplary apparatus. For example, in FIGS. 3 and 4a-c, the apparatus may include an opaque bottle 10b. The bottle 10b may have a substantially airless chamber 11 in which the concentrate and the hydrator may be mixed (shown in FIGS. 4a-c). By protected it from air and light, the chamber increases the stability of the mixture over time and reduces its degradation rate.

In another example (shown in FIGS. 5a-c), the concentrate and hydrator may be provided in separate vessels 22 and 26, such as the illustrated dual tubes with corresponding dual pumps 24 and 28. These may be dispensed simultaneously into the customers' hand and blended manually (FIGS. 5b-c). The customer may emulsify the system by rubbing the systems together in their hands. This agitation has a similar effect to shaking the two phases together in a jar.

These exemplary packaging options may reduce the number of pieces in the apparatus and provide both extra convenience to the customer and a reduced cost to ship (reduced volume in transit). Because the end user may activate the emulsion just before use, the potency of the product may be increased or sustained. As noted above, when a customer activates a full jar (such as about 30 grams, for example) of a product containing retinol, the product begins to degrade immediately and could be about 10% less effective within about 30 days. By mixing each single or individual dose in their hands, the user may experience better efficacy. Instructions for single (individual) dosages may be provided.

Other exemplary apparatuses for dispensing various amounts concentrates and hydrators for an individual dosage of an end product are shown in FIGS. 6a-c and 7a-c. In the illustrated embodiments, the third vessels may be squeeze bottles 30 and 40 that dispense varying dosages of the concentrate and hydrator. The first and second vessels may be chambers 32 and 42 that contain the concentrate may be separate from chambers 34 and 44a-b that contain the hydrator. When compressed, the bottles 30 and 40 may dispense corresponding amounts of the concentrate and hydrator, which may be mixed, for example, in the user's hands as illustrated in FIGS. 6b-c and 7b-c.

All documents cited herein are, in relevant part, incorporated herein by reference; the citation of a document is not, however, to be construed as an admission that it is prior art with respect to the present invention. To the extent that there is a conflict between the use of a term in this application and a document incorporated by reference, the meaning or definition in this application should be applied. While particular embodiments of the present invention have been illustrated and described, changes and modifications can be made without departing from the spirit and scope of the invention.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A composition comprising:
   between about 0.1% and about 1% by weight of a vitamin;
   between about 1% and about 2% by weight of sodium polyacrylate;
   between about 1% and about 3% by weight of hydroxypropylcocoate PEG-8 dimethicone;
   between about 0.05% and about 0.12% by weight of a surfactant;
   between about 1% and about 5% by weight of an emollient;
   between about 0.5% and about 4% by weight an antioxidant; and
   at least about 60% by weight of water.

2. A composition comprising:
   between about 0.5% and about 5% by weight of a vitamin;
   between about 1% and about 4% by weight of polyacrylamide;
   between about 0.25% and about 3% by weight of hydroxypropylcocoate PEG-8 dimethicone;
   between about 0.05% and about 0.12% by weight of a surfactant;
   between about 0.5% and about 2% by weight of an emollient;
   between about 0.5% and about 4% by weight of an antioxidant; and
   at least about 60% water.

3. The composition of claim 1, where the vitamin is one selected from the group consisting of retinol, tocopherol, retinyl palmitate, vitamin C, ascorbyl palmitate, ascorbic acid, L-ascorbic acid, ascorbyl glucoside and 3-ethyl-ascorbic acid.

4. The composition of claim 2, where the vitamin is one selected from the group consisting of retinol, tocopherol, retinyl palmitate, vitamin C, ascorbyl palmitate, ascorbic acid, L-ascorbic acid, ascorbyl glucoside and 3-ethyl-ascorbic acid.

* * * * *